United States Patent [19]

Futch, Sr.

[11] Patent Number: 5,458,603
[45] Date of Patent: Oct. 17, 1995

[54] ELONGATED DRIVE TOOL FOR PROSTHESIS IN BODY CAVITY

[76] Inventor: William A. Futch, Sr., 5490 Hood Rd., Palm Beach Gardens, Fla. 33418

[21] Appl. No.: 177,660

[22] Filed: Jan. 5, 1994

Related U.S. Application Data

[63] Continuation-in-part of Ser. No. 60,599, May 12, 1993, abandoned.

[51] Int. Cl.$^6$ ................................................. A61B 17/88
[52] U.S. Cl. ................................. 606/104; 74/421 R
[58] Field of Search .................................. 433/173, 174, 433/141, 147; 606/104; 81/57.3; 74/421 R; 279/156, 157, 125, 94

[56] References Cited

U.S. PATENT DOCUMENTS

| | | | |
|---|---|---|---|
| 322,937 | 7/1885 | Hungerford | 81/57.3 |
| 2,830,479 | 4/1958 | Finn | 81/57.3 |
| 3,055,272 | 9/1962 | Zwick | 279/157 X |
| 4,374,480 | 2/1983 | Diaz | 74/421 R |
| 5,129,823 | 7/1992 | Hughes | 433/141 |
| 5,236,359 | 8/1983 | Myers et al. | 433/141 |

OTHER PUBLICATIONS

Sales Brochure, R & S Innovations, Inc. The AS 123 Implant Installation System.

*Primary Examiner*—Tamara L. Graysay
*Attorney, Agent, or Firm*—Norman Friedland

[57] ABSTRACT

A surgical instrument which allows the surgeon to insert the instrument in a remote location in a body cavity and from the proximal end rotate a control knob to rotate a tool bit mounted on the distal end for use in prostheses. The surgical instrument can be held in one hand and the control knob can be manipulated by the thumb or finger(s) of that hand. Several drive mechanisms including a spur gear train, bevel gear, spherical ball and link chain and belt are disclosed.

7 Claims, 8 Drawing Sheets

ELONGATED DRIVE TOOL FOR PROSTHESIS IN BODY CAVITY

This application is a continuation-in-part of application Ser. No. 08/060,599, filed May 12, 1993, now abandoned.

1. Technical Field

This invention relates to surgical instruments and particularly to a surgical instrument that is useful in procedures that involve prostheses.

2. Background Art

In more recent years the practice of using implants for securing denture has become or is becoming increasingly popular. The fitting of implant cylinders into the bone and integrating the bone to the material of the implant cylinders by osseointegration, for example, requires several procedures before the denture is inserted into place. The implant, whether submerged or not submerged requires a procedure that necessitates installing and removing certain removable assemblies prior to the installation of the denture. To accommodate the insertion and removing of these assemblies typically requires a tool that must engage a slot in the screw or spline or the like in the assembly to perform these tasks. The instruments that are generally available require that the surgeon or whoever is performing the procedure must insert the instrument into the body cavity, the mouth being the case of the denture, or other body cavities for other protheses, without traumatizing the patient while assuring that the assembly is precisely installed or removed. Additionally the performance of such tasks must not incur any disruption or adversely affect the implant cylinder or subassembly as the case may be. In the case of the denture, for example, where the implant is in proximity to the molars, with present day instruments, the surgeon must insert a portion of his hand into the cavity to gain access to the assembly in order to perform these tasks. This obviously impairs his vision and not only makes his tasks more difficult but misalignment of components is more likely to occur. Examples of these tasks include the insertion of and removal of sealing screws, placement heads, second phase sealing screw, transmucosal implant extension, intromobile element, etc.

I have found that I can provide a surgical tool that will support the instruments for performing the tasks for the insertion and removal of implant sets, for example, that eliminate or minimize the necessity of the surgeon to insert his hand into the cavity for precise removal and insertion while also assuring comfort to the patient.

Of importance the surgical tool is operable with one hand by including a control or drive handle that is capable of being operated by the fingers on the same hand supporting the surgical tool. To assist in this feature the handle is bent to flare upwardly from the upper face of the tool which is on the back side of the face from where the handle extends. It is contemplated that the tool bit that fits in the tool chuck or holder can enter only through the upper face of the surgical tool so that it is impossible to fall out when used with the upper face in the up position relative to ground or the patient. A slidable latch on the upper face of the surgical tool serves to hold the tool bit in place free from axial movement and from falling out when turned in any other attitude. The surgical tool is hermetically sealed and includes means to release steam if water or moisture is trapped on the insides of the surgical tool when subject to heat while being sterilized. A safety valve will pop in the event the internal pressure exceeds a predetermined value. In the event it is necessary to temporarily hold the screw or other component used in the implant process to obtain the initial positioning thereof, a flexible and resilient three pronged annular metallic member fixed to the chuck functions for this purpose.

SUMMARY OF THE INVENTION

An object of this invention is to provide an improved surgical instrument for insertion and removal of component parts involved in prostheses.

A feature of this invention is to provide in a surgical instrument as described an elongated support adapted to rotary support at the distal end a removable insertion or removal tool and a control knob at the proximal end adjacent the handle that is engageable by the fingers or thumb on the hand holding the instrument and a gear train extending between the tool bit and the control knob. In one embodiment the control knob is located on the same face as the tool bit holder and the handle of the surgical instrument is flared upwardly from the upper face remote from the face of the tool bit holder and control knob to facilitate one hand use of the surgical tool.

Another feature of this invention is hermetically sealing the main body of the surgical instrument and to provide means for releasing moisture that may have been inadvertently trapped during autoclaving when the internal pressure reaches a predetermined value. The tool bit is insertable only from the upper face and the chuck is judiciously sized to assure that the tool bit cannot fall out when the tool is held in the upper face facing up relative to ground.

A metallic three pronged holding mechanism attached to the tool bit and chuck to temporarily hold the screw or other abutment being inserted for the initial positioning thereof.

Another feature of this invention is to provide driving mechanism that includes a teethed belt, spherical ball and link chain, or a mitered or bevelled gear as alternative embodiments.

The foregoing and other features of the present invention will become more apparent from the following description and accompanying drawings.

BEST MODE FOR CARRYING OUT THE INVENTION

While the preferred embodiment of this invention being described is utilized in the procedure for installing dentures on implants, as will be understood by those skilled in this art this invention has utility in procedures for other prostheses.

Figure 1:
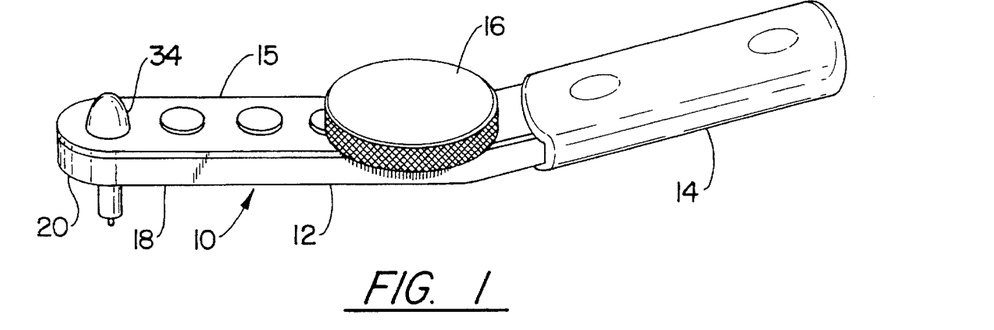
FIG. 1 is a perspective view of the present invention.
Figure 2:
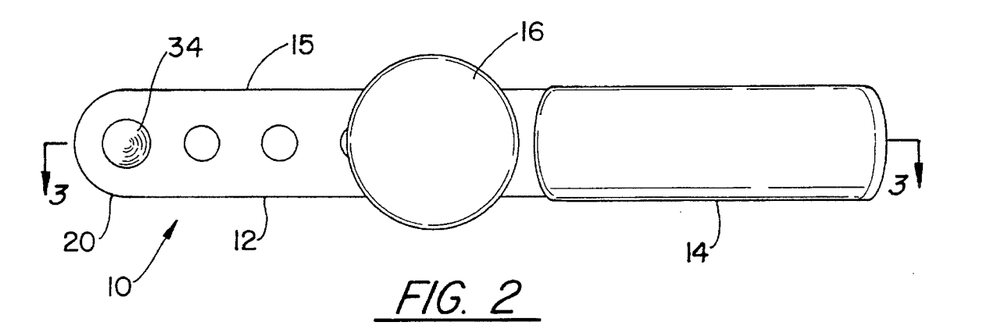
FIG. 2 is a top plan view of the surgical instrument of FIG. 1.

As best seen, FIG. 1 is a perspective view of the preferred embodiment of this surgical instrument generally indicated by reference numeral 10 which is comprised of a relatively rectalinearly shaped main body 12 slightly bent upwardly at the proximal end and necked down to be adapted to support a suitable handle 14. A control knob 16, which will be described in more detail herein below, is rotatably mounted adjacent handle 14 to allow the operator to grasp the instrument in one hand and manipulate the handle with either the thumb or finger of that hand, leaving the other hand free. The edge of the control knob 16 may be knurled to facilitate its movement.

As seen in FIGS. 1–7, the main body 12 includes a top plate 15, bottom plate 18, that is bent upwardly at the distal end and side edges to engage the end and edges of the top plate 15. As noted from FIG. 3 the top plate 15 and bottom plate 18 are parallelly disposed and spaced relative to each other to define an elongated enclosed channel 22. The main body 12 is configured to facilitate being inserted into the mouth cavity, in this instance, but may be tailored to fit other cavities as well. The distal end 20 is slightly curved to avoid any sharp edges that may cause discomfort or injury to the patient.

Figure 3:
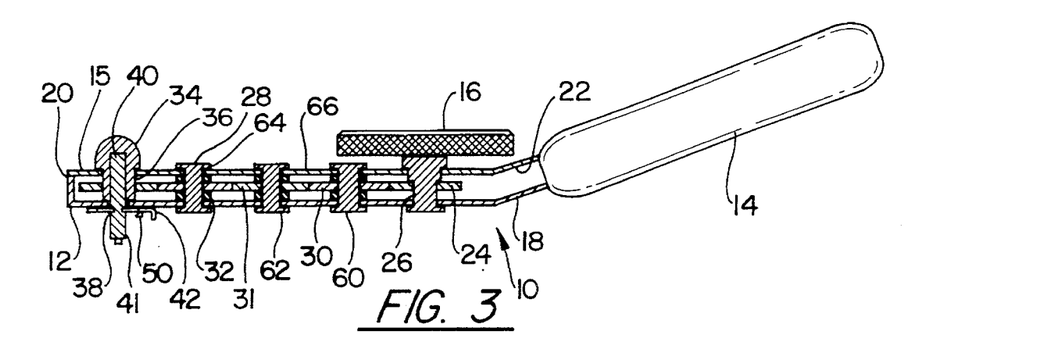
FIG. 3 is a sectional view partly in elevation taken along lines 3—3 of FIG. 2.
Figure 4:
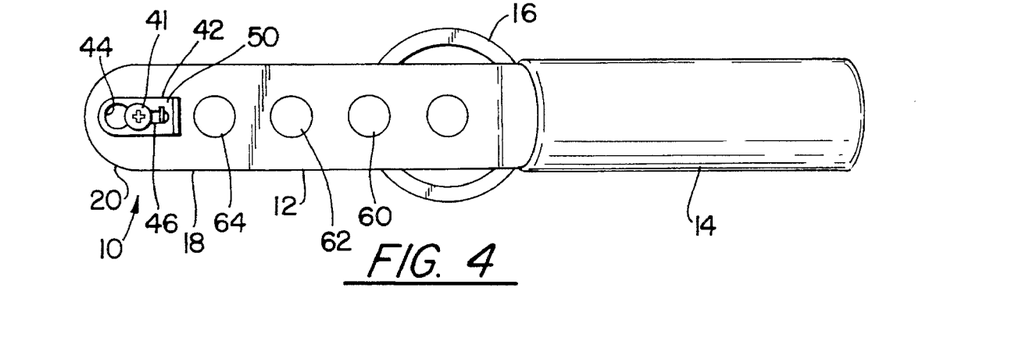
FIG. 4 is a bottom plan view of the surgical instrument depicted in FIG. 1.
Figure 5:
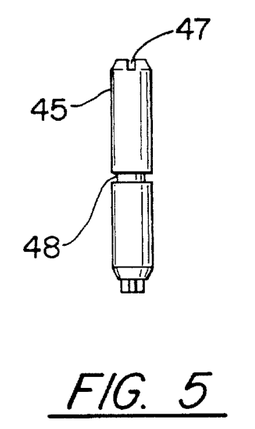
FIG. 5 is a view in elevation of the tool bit.
Figure 5A:
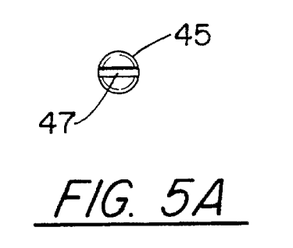
FIG. 5A is a top plan view of the tool bit.

A plurality of spur gears are suitably rotatably supported in channel 22 to form a gear train so as to rotate the tool or tool bit 41 that is mounted on the distal end 20 by virtue of the rotation of control knob 16 which is mounted on the proximal end. The driving gear 24 which is rigidly fixed to shaft 26 and rotatable therewith which in turn is fixed to control knob 16 drives driven gear 28 via the idler gears 30, 31 and 32. Gear 28 is suitably fixed, say by brazing, to the rotatable tool holder 34. Tool holder 34 consist of a collar 36 extending through aligned apertures 35 and 37 formed in top plate 15 and bottom plate 18, respectively, and an enlarged head portion 39 that shoulders against the top surface of top plate 15. A central bore 38 formed in collar 36 is adapted to receive the tool bit 41. A tang 40 formed at the end of the bore 38 adjacent the head portion 39 is adapted to fit into a complementary slot formed on the tool bit 41. This serves to rotate the tool bit 41 with rotational movement of the tool holder 34.

Figure 6:
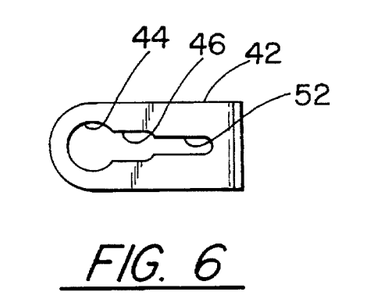
FIG. 6 is a plan view of the tool retaining clip.
Figure 7:
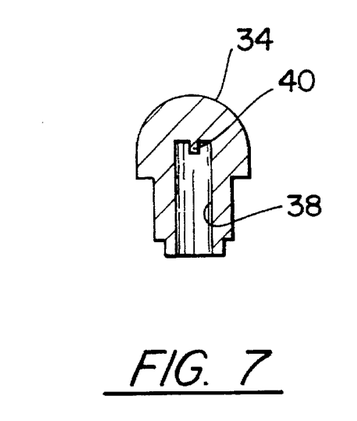
FIG. 7 is a sectional view of the tool holder.
Figure 7A:
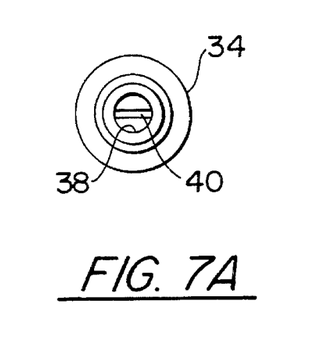
FIG. 7A is a bottom plan view of the tool holder.

A tool retainer clip 42 is slidably mounted on the bottom plate 18 adjacent central bore 38 and has formed therein a hole 44 at least equally sized to the diameter of the central bore 38 to allow passage of the tool bit 41 carrying slot 47 at the top end to be inserted into the central bore to engage tang 40, and a reduced sized slot 46 that fits into an annular groove 48 formed in the tool bit 41. The pin 50 suitably attached to the bottom plate 18 slidably supports the tool retaining clip 42 through axial slot 52 that interconnects hole 44 and slot 46 to allow the retainer clip 42 to align hole 44 and slot 46 to insert, remove and retain the tool bit 41.

Idler gears 30, 31 and 32 are supported in channel 22 by stub shafts 60, 62 and 64, respectfully and each stub shaft may include a bushing 66 to assure free rotation of the idler gears. Each stub shaft is suitably supported in the bottom plate 18 and top plate 15.

In operation, the surgeon would hold the surgical instrument 10 by handle 14 and insert the distal end 20 into the cavity where the operation is being performed. By rotation of the control knob 16 with the thumb [or finger(s)] of the same hand, the removable tool bit 41 will follow the rotational movement, inserting or removing the device or assembly, as the case may be.

It is contemplated within the scope of this invention, that control knob 16 may include a slip clutch that would slip when the torque exerted on the member being inserted attains a desired torque. An adjustable spring on the slip clutch would determine the torque. Additionally the instrument could include a well known counter that would count the number of rotations the tool bit 41 makes. Obviously the instrument would select the gears with the desired number of teeth to obtain the gear reduction desired.

Figure 8:
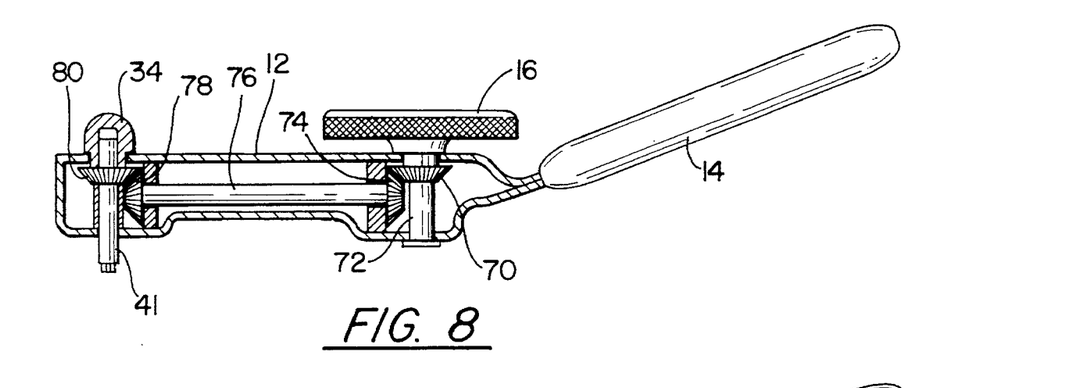
FIG. 8 is a view partly in elevation and partly in section illustrating another embodiment of this invention where a bevel gear is utilized.
Figure 9:
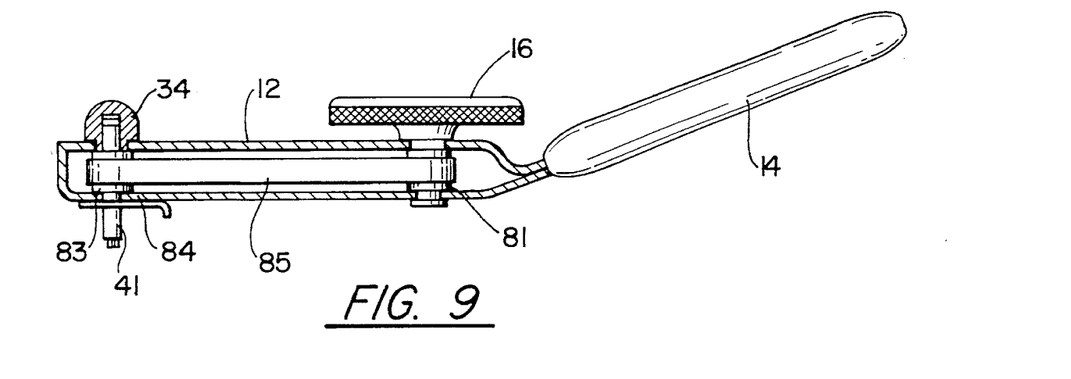
FIG. 9 is a view partly in section and partly in elevation illustrating another embodiment of this invention where a belt is utilized.
Figure 10:
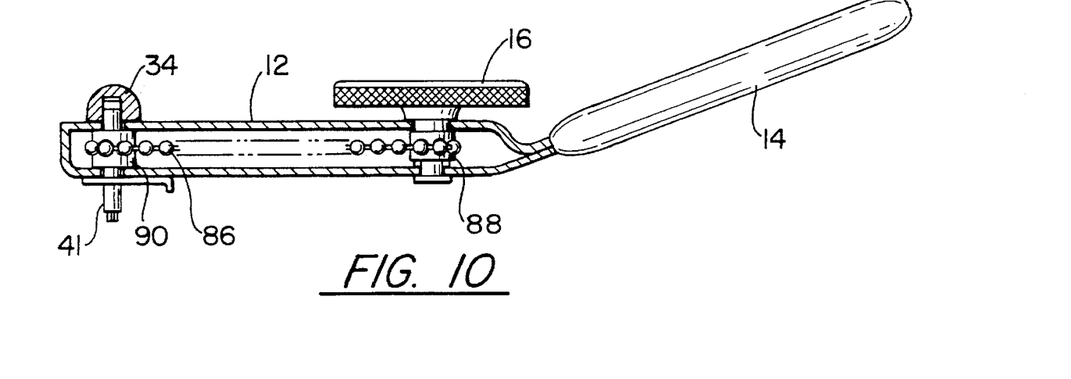
FIG. 10 is a view partly in section and partly in elevation illustrating another embodiment of this invention where a sprocket and spherical ball and link chain is utilized.
Figure 11:
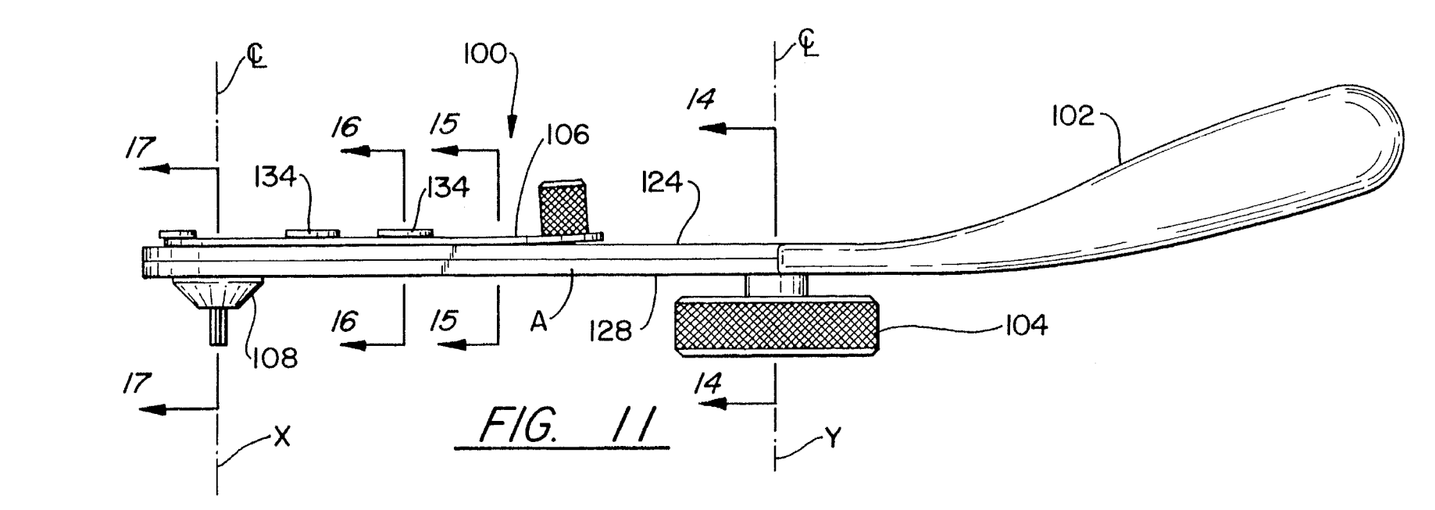
FIG. 11 is a side elevation view exemplifying another embodiment of this invention.
Figure 12:
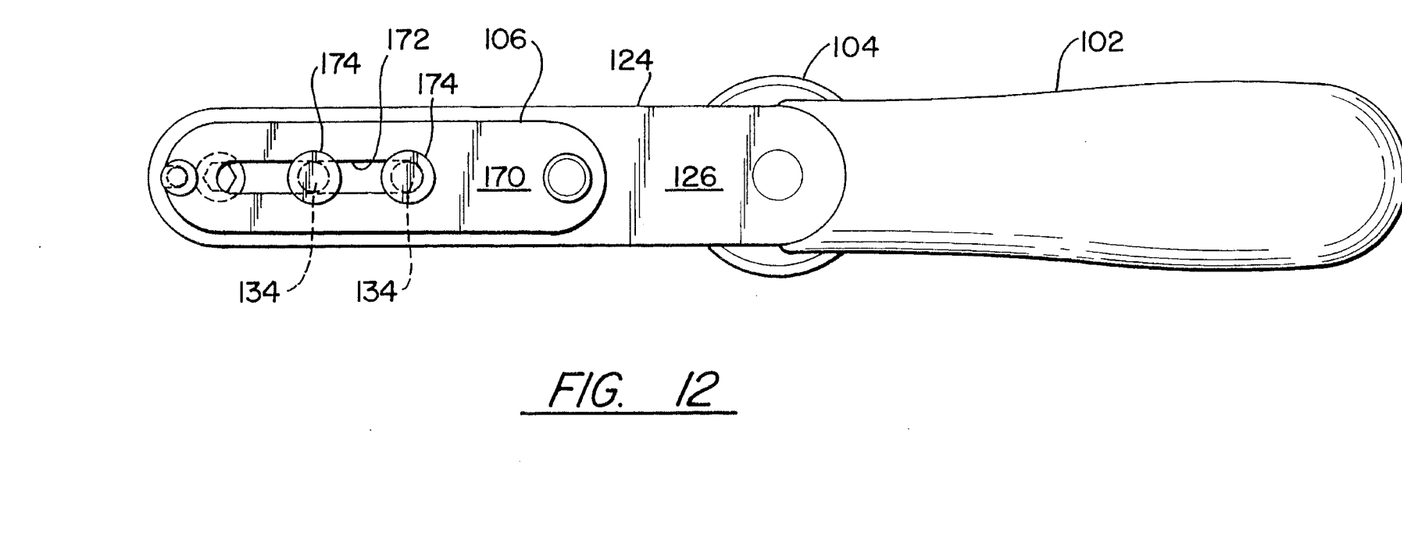
FIG. 12 is a top plan view of the embodiment depicted in FIG. 11.
Figure 13:
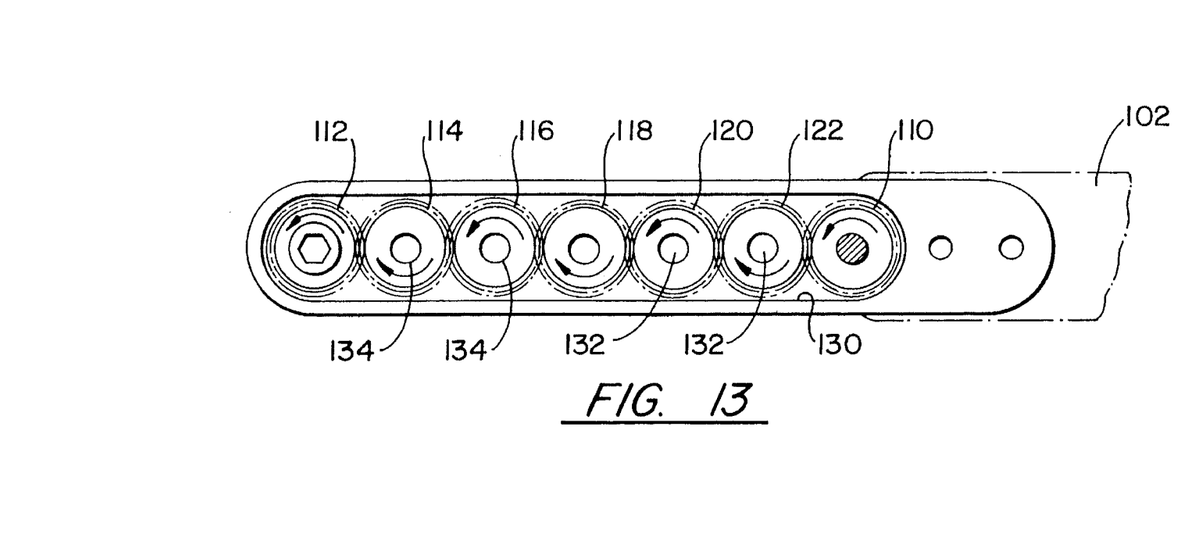
FIG. 13 is a top view of FIG. 1 with the top plate removed to show the drive gear arrangement.
Figure 14:
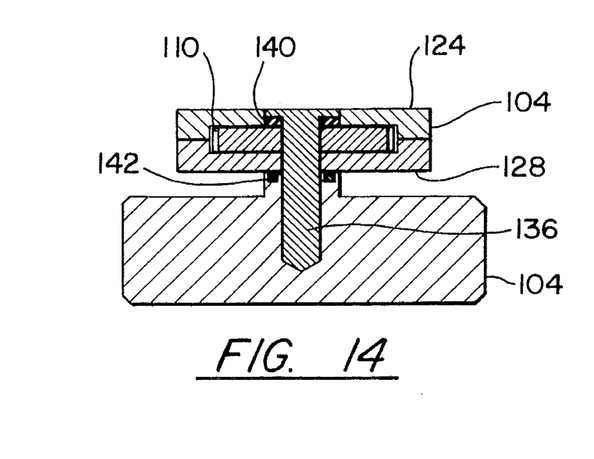
FIG. 14 is a sectional view taken through lines 14—14 of FIG. 11.
Figure 15:
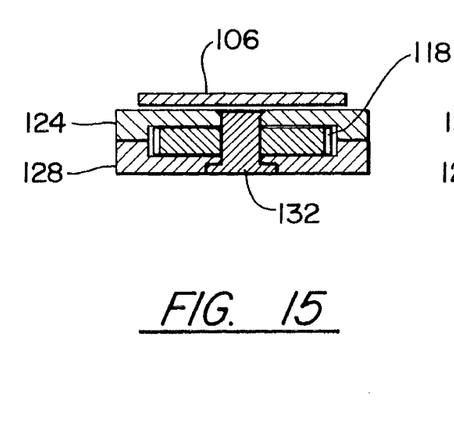
FIG. 15 is a sectional view taken through lines 15—15 of FIG. 11.
Figure 16:
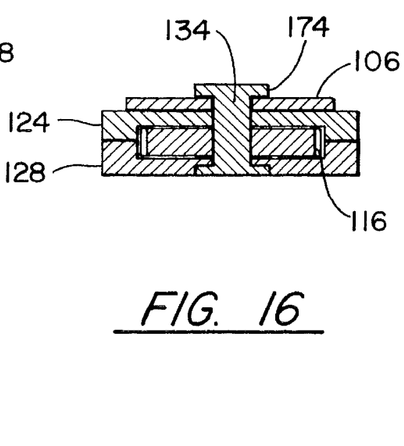
FIG. 16 is a sectional view taken through lines 16—16 of FIG. 11.
Figure 17:
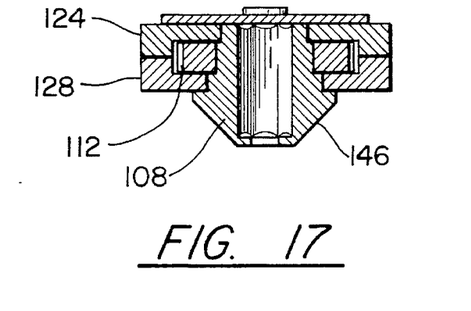
FIG. 17 is a sectional view taken through lines 17—17 of FIG. 11 illustrating the chuck of this invention.

FIGS. 8–9 exemplify three different drive mechanisms that can be substituted for the gear train described immediately above. In FIG. 8 bevel gear 70 is attached to shaft 72 of control knob 16 (like reference numerals designate like elements in all the Figs.) and rotates therewith. Bevel gear 74 meshes with bevel gear 70 and is attached to shaft 76 which carries bevel gear 78 that, in turn, meshes with bevel gear 80 that is rigidly secured to collar 36 of tool holder 34. In FIG. 9 the drive mechanism may include pulleys 81 and 83 (tooth type) attached to the control knob shaft and collar of tool holder 34. The pulleys 81 and 83 are interconnected by a suitable belt 85 (toothed) for attaining the rotary motion. In FIG. 10 the drive mechanism includes a spherical ball and link chain 86 that is driven by complementary pulleys 88 and 90 to attain the rotary motion.

FIGS. 11–22 discloses a number of views exemplifying another embodiment the elongated drive tool of this invention which consists of the main body 100, handle 102, control knob 104, latching mechanism 106, chuck 108, the gear train including the drive gear 110, driven gear 112 and the idler gears 114, 116, 118, 120 and 122. The number of gears are selected to achieve the desired length of the main body 100 of the elongated drive tool and to assure that the direction of rotation is the same for the linearly disposed input and output, i.e, the drive gear 110 and driven gear 112. Similar to the design of the embodiment depicted in FIG. 1, this embodiment includes an upper elongated flat plate 124 having a planar exterior upper or top surface 126 and a matching lower elongated housing 128 having an interior recess 130 only opened at the top to accommodate the gear train and having a planar exterior lower surface. The top plate 124 overlies the bottom housing 128 and covers the recess 130 and includes a mating planar interior surface that mates with the upper interior surface of bottom housing 128. These mating surfaces are lap fitted along the parting plane A in order to define a contiguous metal to metal contact that serves to hermetically seal the recess 130. The top plate 124 and bottom housing 128 are held together by a plurality of conventional rivets 132 and 134 which are peened into place. In addition to holding the two halves of the elongated drive tool together, these rivets serve as shafts for the idler gears 114, 116, 118 ,120 and 122. The two (2) rivets 134 extend beyond the upper surface 126 for supporting the latch 106 as will be described in further detail hereinbelow.

The control knob 104 is rigidly connected to the drive gear 110 by stub shaft 136 extending transversely relative to the elongated housing 128 is journeled in top plate 124 and bottom housing 128 for rotary motion. Obviously, rotation of control knob 104 results in a like rotation of linearly spaced driven gear 112 which, as will be explained immediately below, is attached to chuck 108. Seals 140 and 142, which may take the form of suitable O-rings serve to prevent leakage into the recess 130 along the stub shaft 136.

Figure 18:
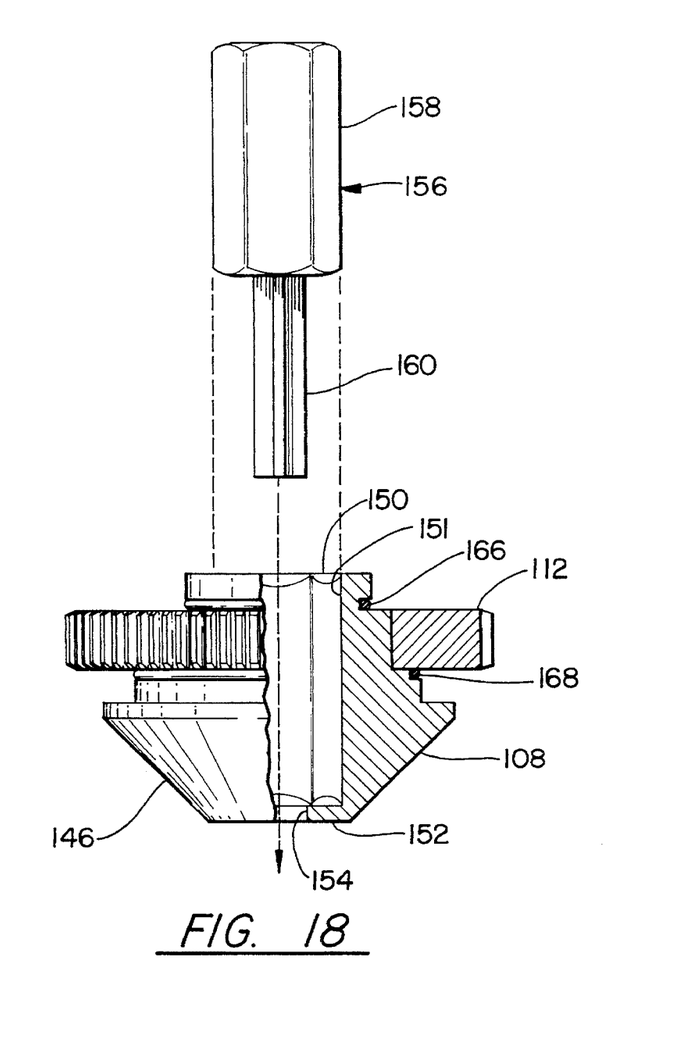
FIG. 18 is an exploded view in section and elevation illustrating the relationship of the tool bit and chuck.
Figure 19:
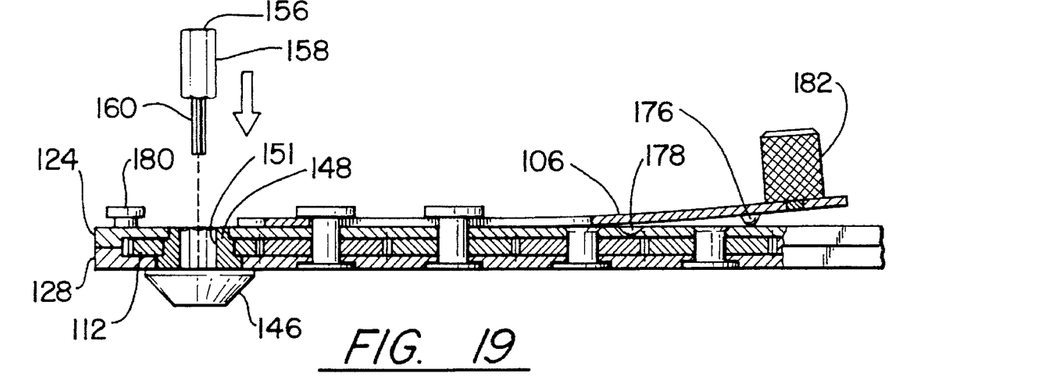
FIG. 19 is an exploded view in section and elevation illustrating the sliding latch mechanism for supporting the tool bit in place.
Figure 20:
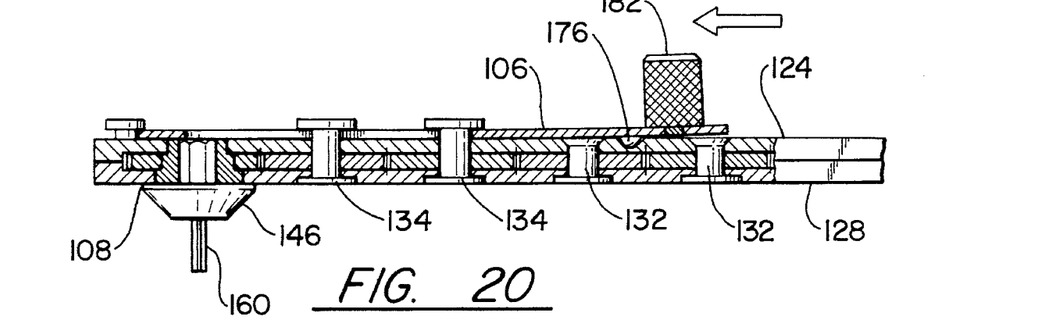
FIG. 20 illustrated the tool bit in situ and the latch positioned to the locked position.
Figure 21:
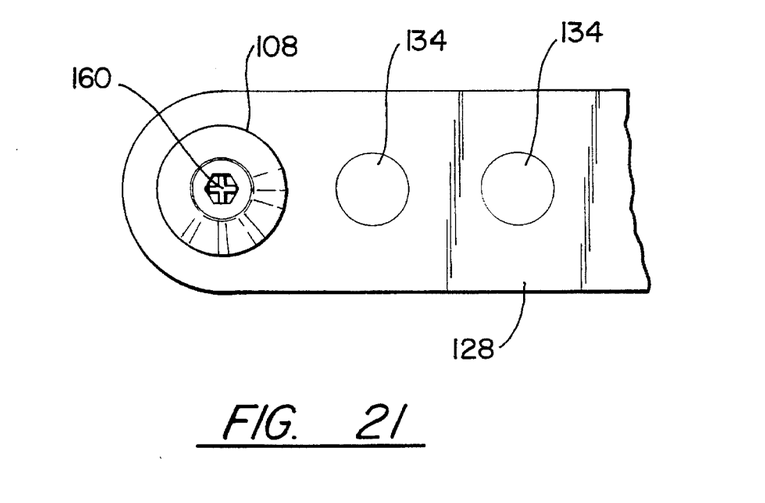
FIG. 21 is a partial bottom plan view illustrating the tool bit.
Figure 22:
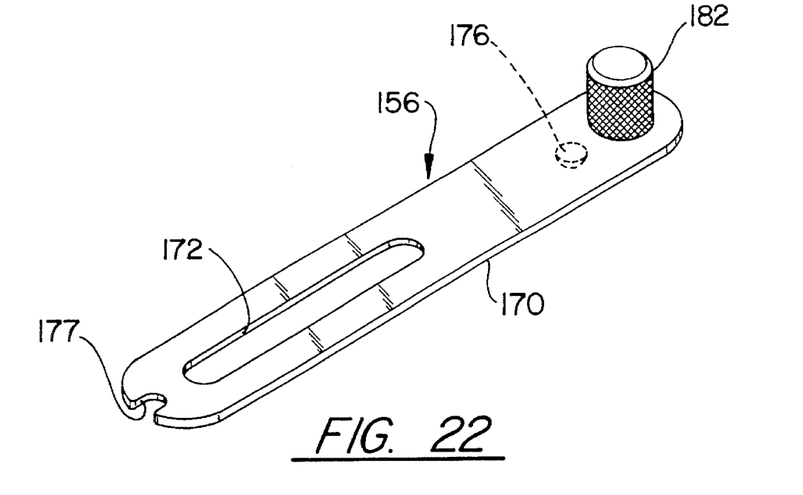
FIG. 22 is a perspective view of the latching mechanism.

Chuck 108 includes a tapered end 146 and a stepped reduced diameter shank 148. Driven gear 112 is firmly affixed to shank 148 which is journaled in the top plate 124 and the bottom housing 128 and rotates therewith. Chuck 146 contains a central polygonal shaped bore 151 extending from the top edge 150 to just short of the bottom edge 152. A smaller diameter central drilled hole 154 extends from the bottom edge 152 to communicate with the bore 151. As can be seen in FIG. 18 the tool bit 156 includes the larger diameter shank portion 158 that is polygonally shaped to complement the shape of bore 151 so as to rotate therewith and the working portion or smaller diameter portion 160 of tool bit 156 is sized to snugly pass through the drilled hole 154. Obviously the shape of the end of the tool bit is contoured to fit into the screw or abutment being inserted or removed in the implant process. Seals 166 and 168, which may take the form of O-rings serve to prevent leakage into the recess 130 along the outer surface of chuck 108.

The tool bit 156 is held in place and preloaded by the latch 106 that includes an elongated flat member 170 mounted in sliding relationship relative to the top surface 126 and is formed from a suitable metallic spring material that is flexible and resilient such as stainless steel. Slot 172 formed in latch member 170 serves as a guide for sliding the latch axially relative to the elongated top surface 126. Rivets 134, preferably two (2), extend slightly beyond the top surface 126 extend through slot 172 and the diameter of the rivets are sufficiently large to keep the latch from moving out of alignment. The heads 174 of the two rivets 134 are slightly enlarged to extend laterally beyond the slot 172 to overlie the top surface of member 170. A detent 176 extending from the bottom surface of member 170 fits into a dimple 178 formed in the top surface 126 of plate 124 at the end of its travel when locking tool bit 156 in place. Notch 177 formed at the end of latch 106 fits into headed pin 180 which transversely extends from the top surface 126 and underlies the head of pin 180 when the latch is deployed. This serves to hold the latch from moving upwardly to counteract the force exerted on the tool bit when in operation. A suitable knob 182 which may be knurled is attached to the end of latch 106 to facilitate the sliding movement of latch 106. As noted in FIG. 9 the end of latch 106 when moved away from the deployed position lifts up and since this is fabricated from spring material the energy stored in this movement is transferred to the opposite end to bear against the top surface of the tool bit.

Although other blow off valves may be employed to release the pressure occasioned by heating the instrument that may have inadvertently obtained trapped moisture, according to this invention the thickness of the wall beneath the detent 178 is judiciously selected to burst upon the internal pressure reaching a predetermined value.

From the foregoing it will be appreciated that the tool bit can only be inserted through the top plate 124 and cannot fall out through the bottom plate owing to the sizes of the stepped tool bit and the drilled hole 154. A multitude of various tool bits are designed to have like polygonal shanks for use with the elongated drive tool for accommodating various screws or other abutments.

Rotation of control knob 104 will effectuate a 1 to 1 ratio and rotate the laterally spaced tool bit 156 in the same direction. Of course other ratios can be selected by varying the gear ratio of the gear train. Because of the location and size of control knob 104 and the relative location and angle of handle 102, one hand use of the tool is realized, which of course frees the other hand to allow the operator to use it for other purposes. Hence, the elongated drive tool serves as an offset screw driver with the chuck and control handle extending from the same planar surface, rotates about their laterally spaced and parallelly disposed rotational axes X and Y, respectively. As this tool is intended for surgical use the components are fabricated from a suitable material that is capable of withstanding the heat for disinfecting purposes such as stainless steel of surgical quality.

Figure 23:
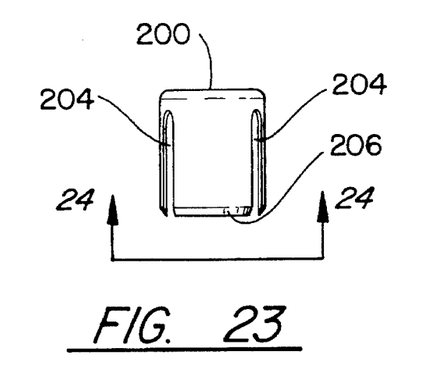
FIG. 23 is a view in elevation of the retaining sleeve for supporting screws and abutments for initial positioning.
Figure 24:
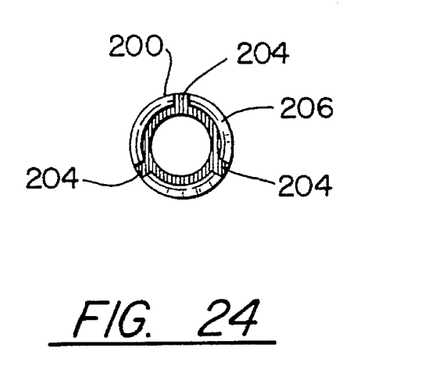
FIG. 24 is a bottom plan view of the retaining sleeve of FIG. 23.
Figure 25:
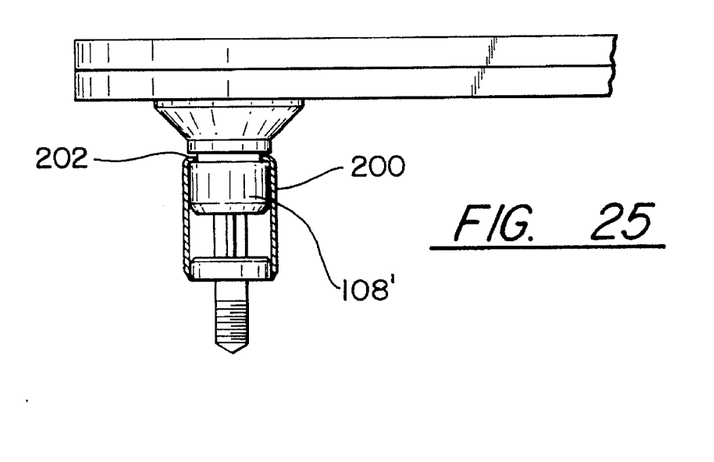
FIG. 25 is a partial view partly in section and partly in elevation illustrating the retaining sleeve in situ.

FIGS. 23–25 illustrate a cylindrical sleeve 200 that serves to hold a screw or abutment in axial alignment with the tool bit to initiate the operation of insertion or removal from the implant process. Sleeve 200 is suitably attached to chuck 108', which is similar in design as chuck 108 except for the exterior configuration that serves to accommodate sleeve 200. The upper end of sleeve 200 is bent or spun in situ to extend radially inwardly toward the axes A defining flange 202 that fits in an annular groove formed in the outer periphery of chuck 208' or could fit into an space between the bottom exterior planar surface of bottom housing 128 and the chuck 208'. The fit of the sleeve is such that it is restrained from axial movement and rotates with the chuck while the screw and abutment is initiating its engagement. Once the screw and abutment is released from the sleeve 200, there is sufficient tolerance to allow the sleeve to stop rotation. This is in consideration of the patient to avoid discomfort. The screw or abutment are held by fingers 206 formed in sleeve 200 by three axially extending slots 204. The material preferred for the sleeve 200 is stainless steel (surgical quality) that is sufficiently rigid and resilient to hold the screw or abutment, yet capable of releasing it after it is inserted a short distance. Various shaped retaining sleeves to match different sized screws and abutments are contemplated.

Although this invention has been shown and described with respect to detailed embodiments thereof, it will be appreciated and understood by those skilled in the art that various changes in form and detail thereof may be made without departing from the spirit and scope of the claimed invention.

I claim

1. Surgical instrument apparatus for insertion in a body cavity comprising an elongated housing having a top wall, bottom wall, opposing side walls, a proximal end and a distal end defining an enclosed elongated chamber, a handle supported to the proximal end of said elongated housing and extending axially and angularly upward relative to said top wall, a control knob, means extending from said bottom wall for supporting said control knob in said elongated housing adjacent the proximal end for rotatable motion and adapted to be engagable by the thumb and finger of the same hand of the operator holding said handle, said means including a first shaft supported in said elongated housing and transversely extending through said chamber relative to the longitudinal axis of said elongated housing, a drive gear fixed to said first shaft disposed in said chamber and rotatable therewith, a chuck disposed adjacent to said bottom wall, means including a second shaft extending transversely through said elongated housing for rotatably supporting said chuck to said housing, a driven gear disposed in said chamber attached to said second shaft for rotating said chuck, at least one idler gear including a stub shaft to support said idler gear in said chamber and meshing with said driven gear and said drive gear for transmitting rotary motion, a tool supported in a central bore formed in said chuck and adapted to be removed, said tool having a larger diameter portion disposed in said central bore and a narrower working portion extending through a smaller diameter formed at the end of said chuck such that the tool is only inserted through an upper end of said chuck means, a latch, a pin extending upwardly from said top wall and extending through an elongated slot in said latch for supporting said latch on the top wall of said elongated housing, said latch for sliding over said tool to secure said tool in the central bore of said chuck, whereby said tool can not fall out the upper end of said chuck when held in any attitude, and when said distal end of said housing and said tool are positioned in the body cavity, said tool is rotated in said chuck as a function of said control knob to perform a procedure due to the meshing of said drive gear, idler gear and driven gear to a prosthesis assembly.

2. Surgical instrument apparatus as claimed in claim 1 wherein said drive gear is a drive spur gear disposed in said chamber attached to said shaft, said driven gear is a driven spur gear in said chamber and said idle gear is a spur idler gear in meshing relationship with said drive spur gear and said driven spur gear.

3. Surgical instrument apparatus as claimed in claim 2 wherein said one idler gear includes five idler gears each having a stub shaft in meshing relationship relative to said drive gear and said driven gear.

4. Surgical instrument apparatus as claimed in claim 3 wherein said bottom wall, said opposing side walls, said proximal end and said distal end define an open top elongated chamber; the top surface of said opposing side walls, said proximal end and said distal end is lap fitted to an outer peripheral edge of a bottom surface of said top wall; and, seal means are disposed relative to said first shaft adjacent to said top wall and adjacent to said bottom wall and disposed relative to said second shaft adjacent to said top wall and adjacent to said bottom wall for hermetically sealing said elongated chamber.

5. Surgical instrument apparatus as claimed in claim 4 wherein at least two of said stub shafts comprise axially spaced rivets for attaching said top wall to said bottom wall and extending through central apertures in said idler gears for supporting said idler gears for rotary motion, wherein said idler gears are rotatably supported by rivet means securing said top wall to said bottom wall.

6. Surgical instrument apparatus as claimed in claim 5 wherein said latch includes a detent formed on the bottom surface for fitting into a dimple formed on the top surface of said top wall for locking said latch when overlying said tool, a headed pin extending transversely relative to said latch for engaging a notch formed on the forward end of said latch when overlying said tool and a latch handle extending transversely relative to said latch adapted to position said slidable latch when overlying said tool and spaced away from said tool.

7. Surgical instrument apparatus as claimed in claim 6 including a retaining sleeve attached to said chuck and concentrically disposed relative thereto, at least three fingers extending axially relative to said chuck adapted to temporarily hold a screw for alignment thereof and adapted to be released from the screw.

\* \* \* \* \*